United States Patent
Sivasubramanian et al.

(10) Patent No.: US 9,528,922 B2
(45) Date of Patent: Dec. 27, 2016

(54) SYSTEM AND METHOD FOR DETERMINING THE SPECIFIC GRAVITY OF A GASEOUS FUEL

(71) Applicant: Caterpillar Inc., Peoria, IL (US)

(72) Inventors: Arvind Sivasubramanian, Peoria, IL (US); Christopher Gallmeyer, Chillicothe, IL (US); Venkat Vijay Kishore Turlapati, Peoria, IL (US); Brett Zook, Cutler, IN (US); Jason Rasmussen, Hopewell, IL (US)

(73) Assignee: Caterpillar Inc., Peoria, IL (US)

( * ) Notice: Subject to any disclaimer, the term of this patent is extended or adjusted under 35 U.S.C. 154(b) by 269 days.

(21) Appl. No.: 14/311,853

(22) Filed: Jun. 23, 2014

(65) Prior Publication Data
US 2015/0369716 A1    Dec. 24, 2015

(51) Int. Cl.
*G01N 9/26*    (2006.01)
*G01N 33/22*   (2006.01)

(52) U.S. Cl.
CPC .............. *G01N 9/26* (2013.01); *G01N 33/225* (2013.01)

(58) Field of Classification Search
CPC ...... G01N 9/26; G01N 33/225; F02D 41/0025
See application file for complete search history.

(56) References Cited

U.S. PATENT DOCUMENTS

| | | | | |
|---|---|---|---|---|
| 3,701,280 A | * | 10/1972 | Stroman | G01F 15/043 702/45 |
| 3,855,845 A | * | 12/1974 | Homolka | G01N 9/26 73/30.02 |
| 4,134,301 A | * | 1/1979 | Erwin, Jr. | G01F 9/001 73/114.42 |
| 4,285,245 A | * | 8/1981 | Kennedy | G01F 3/38 73/199 |
| 4,380,400 A | * | 4/1983 | Searle | G01N 33/0013 374/37 |
| 4,384,472 A | * | 5/1983 | Tournier | G01N 11/08 73/30.01 |
| 4,677,841 A | * | 7/1987 | Kennedy | G01N 9/32 73/30.02 |
| 4,920,494 A | * | 4/1990 | Abo | F02D 35/023 123/435 |
| 4,942,848 A | * | 7/1990 | Terasaka | F02D 19/0628 123/1 A |
| 4,984,451 A | * | 1/1991 | Wilen | G01N 9/28 73/438 |
| 5,016,482 A | * | 5/1991 | Clingman, Jr. | G01N 33/225 137/100 |

(Continued)

*Primary Examiner* — David Bolduc
(74) *Attorney, Agent, or Firm* — Baker & Hostetler LLP (57) ABSTRACT

The disclosure relates to a system and method for determining the specific gravity of a fuel used in a dual fuel engine. The system includes a fuel rail, at least one sensor, and a processor. The method includes sensing and recording, with the at least one sensor and the at least one memory, a first pressure profile of a first fuel in the fuel rail and a second pressure profile of a second fuel in the fuel rail. The first fuel has a known specific gravity and the second fuel has an unknown specific gravity. The method further includes calculating the second specific gravity of the second fuel, with a processor, based on the first pressure profile, the second pressure profile, and the first specific gravity.

9 Claims, 4 Drawing Sheets

(56) References Cited

U.S. PATENT DOCUMENTS

| | | | | |
|---|---|---|---|---|
| 5,027,768 A * | 7/1991 | Saegusa | | F02D 41/38 |
| | | | | 123/357 |
| 5,115,687 A * | 5/1992 | Clingman, Jr. | | G01N 1/2247 |
| | | | | 73/863.03 |
| 5,323,657 A * | 6/1994 | Vander Heyden | | G01F 1/48 |
| | | | | 374/36 |
| 5,357,809 A * | 10/1994 | Vander Heyden | | G01F 5/00 |
| | | | | 374/36 |
| 5,807,749 A * | 9/1998 | Hornemann | | G01N 33/225 |
| | | | | 374/36 |
| 5,937,800 A * | 8/1999 | Brown | | F02B 7/06 |
| | | | | 123/27 GE |
| 6,058,761 A * | 5/2000 | Vander Heyden | | G01N 9/32 |
| | | | | 73/30.01 |
| 6,226,981 B1 | 5/2001 | Bruch et al. | | |
| 6,612,186 B1 * | 9/2003 | Patten | | G01F 1/84 |
| | | | | 73/861 |
| 6,941,929 B2 | 9/2005 | Shinzawa | | |
| 7,027,906 B2 | 4/2006 | Araki | | |
| 7,028,532 B2 | 4/2006 | Shinzawa | | |
| 7,367,223 B2 | 5/2008 | Kettl et al. | | |
| 7,913,675 B2 | 3/2011 | Bailey et al. | | |
| 2003/0093184 A1 * | 5/2003 | Tanaka | | F02C 9/28 |
| | | | | 700/289 |
| 2004/0154386 A1 * | 8/2004 | Shinzawa | | F02D 19/0628 |
| | | | | 73/114.39 |
| 2004/0154591 A1 * | 8/2004 | Shinzawa | | F02D 19/0628 |
| | | | | 123/406.47 |
| 2004/0261414 A1 * | 12/2004 | Araki | | F02B 75/02 |
| | | | | 60/602 |
| 2005/0065710 A1 * | 3/2005 | Yasuda | | F02D 33/003 |
| | | | | 701/114 |
| 2005/0188948 A1 * | 9/2005 | Miura | | F02D 41/0002 |
| | | | | 123/299 |
| 2010/0162711 A1 * | 7/2010 | Zuo | | F23R 3/286 |
| | | | | 60/742 |
| 2011/0088657 A1 * | 4/2011 | Tanno | | F02D 35/028 |
| | | | | 123/305 |
| 2012/0079831 A1 * | 4/2012 | Kirzhner | | F02C 7/22 |
| | | | | 60/776 |
| 2014/0238032 A1 * | 8/2014 | Fitzgerald | | F02C 9/26 |
| | | | | 60/772 |
| 2014/0366839 A1 * | 12/2014 | Sivasubramanian | | F02D 41/0025 |
| | | | | 123/352 |
| 2014/0366840 A1 * | 12/2014 | Sivasubramanian | | F02D 41/0025 |
| | | | | 123/399 |
| 2015/0226140 A1 * | 8/2015 | Zhang | | F02D 41/0027 |
| | | | | 123/497 |
| 2015/0233310 A1 * | 8/2015 | Zhang | | F02D 19/06 |
| | | | | 701/54 |
| 2015/0345408 A1 * | 12/2015 | Sivasubramanian | | F02D 19/0607 |
| | | | | 123/445 |

* cited by examiner

SYSTEM AND METHOD FOR DETERMINING THE SPECIFIC GRAVITY OF A GASEOUS FUEL

TECHNICAL FIELD

This disclosure relates generally to a system and method for determining specific gravity of a gaseous fuel, and more particularly, to a system and method for determining the specific gravity of an unknown gaseous fuel in a dual fuel engine or a gaseous fuel engine.

BACKGROUND

Dual fuel engines generally run using diesel fuel, gaseous fuel, or both. When an engine is run on gaseous fuel, it is important to maintain the air to fuel ratio to meet emission regulations. The air to fuel ratio of gaseous fuel may be calculated by using the fuel mass flow, which is based on the specific gravity of the gaseous fuel. However, the specific gravity of the gaseous fuel may be unknown.

Current methods for determining the specific gravity of a gaseous fuel include using air and fuel mass quantities. U.S. Pat. No. 7,028,532 (hereinafter "the '532 patent"), assigned to Nissan Motor Co., Ltd., discloses a method for calculating an actual specific gravity of a fuel. It uses a ratio of actual fuel supply weight to the fuel quantity to calculate specific gravity, whereby the fuel quantity is retrieved from a predetermined relationship between fuel quantity, engine speed, and load, and whereby the fuel supply weight is calculated by using an air/fuel ratio and air quantity, both of which are retrieved from tables. Current methods, such as ones described in the '532 patent, require a variety of sensors and relational lookup tables to calculate a specific gravity, each of which may provide a degree of uncertainty.

Thus, a simplified method for determining the specific gravity of a gaseous fuel within a dual fuel system is desired to maintain an air to fuel ratio.

The foregoing background discussion is intended solely to aid the reader. It is not intended to limit the innovations described herein, nor to limit or expand the prior art discussed. Thus, the foregoing discussion should not be taken to indicate that any particular element of a prior system is unsuitable for use with the innovations described herein, nor is it intended to indicate that any element is essential in implementing the innovations described herein. The implementations and application of the innovations described herein are defined by the appended claims.

SUMMARY

An embodiment of the present disclosure includes a method for determining the specific gravity of a fuel used in a dual fuel engine. The method includes sensing and recording a first pressure profile of a first fuel and a second pressure profile of a second fuel with at least one sensor and a least one memory. The first fuel has a known specific gravity and the second fuel has an unknown specific gravity. The method further includes calculating the second specific gravity of the second fuel, with a processor, based on the first pressure profile, the second pressure profile, and the first specific gravity.

Another embodiment of the present disclosure includes a controller for a dual fuel system for calculating the specific gravity of fuel. The controller includes at least one sensor and a processor. The at least one sensor is configured to sense a first pressure profile of a first fuel and second pressure profile of a second fuel. The first fuel has a first specific gravity that is known and the second fuel has a second specific gravity that is unknown. The processor is configured to calculate the second specific gravity of the second fuel using the first pressure profile, the second pressure profile, and the first specific gravity.

Another embodiment of the present disclosure includes a system for calculating the specific gravity of a fuel. The system includes a fuel rail, at least one sensor, and a processor. The fuel rail is configured to contain the fuel within. The at least one sensor is coupled to the fuel rail. The at least one sensor is configured to sense, within the fuel rail, a first pressure profile of a first fuel and a second pressure profile of a second fuel. The first fuel has a first specific gravity that is known and the second fuel has a second specific gravity that is unknown. The processor is configured to calculate the second specific gravity of the second fuel using the first pressure profile, the second pressure profile, and the first specific gravity.

DETAILED DESCRIPTION

The disclosure relates generally to a system and method for determining the specific gravity of a gaseous fuel in a dual fuel engine. The method includes sensing and recording a pressure profile of a fuel having a known specific gravity and sensing and recording a pressure profile of a fuel having an unknown specific gravity. Based on the sensed and recorded pressure profiles and the known specific gravity, the unknown specific gravity may be calculated.

Figure 1:
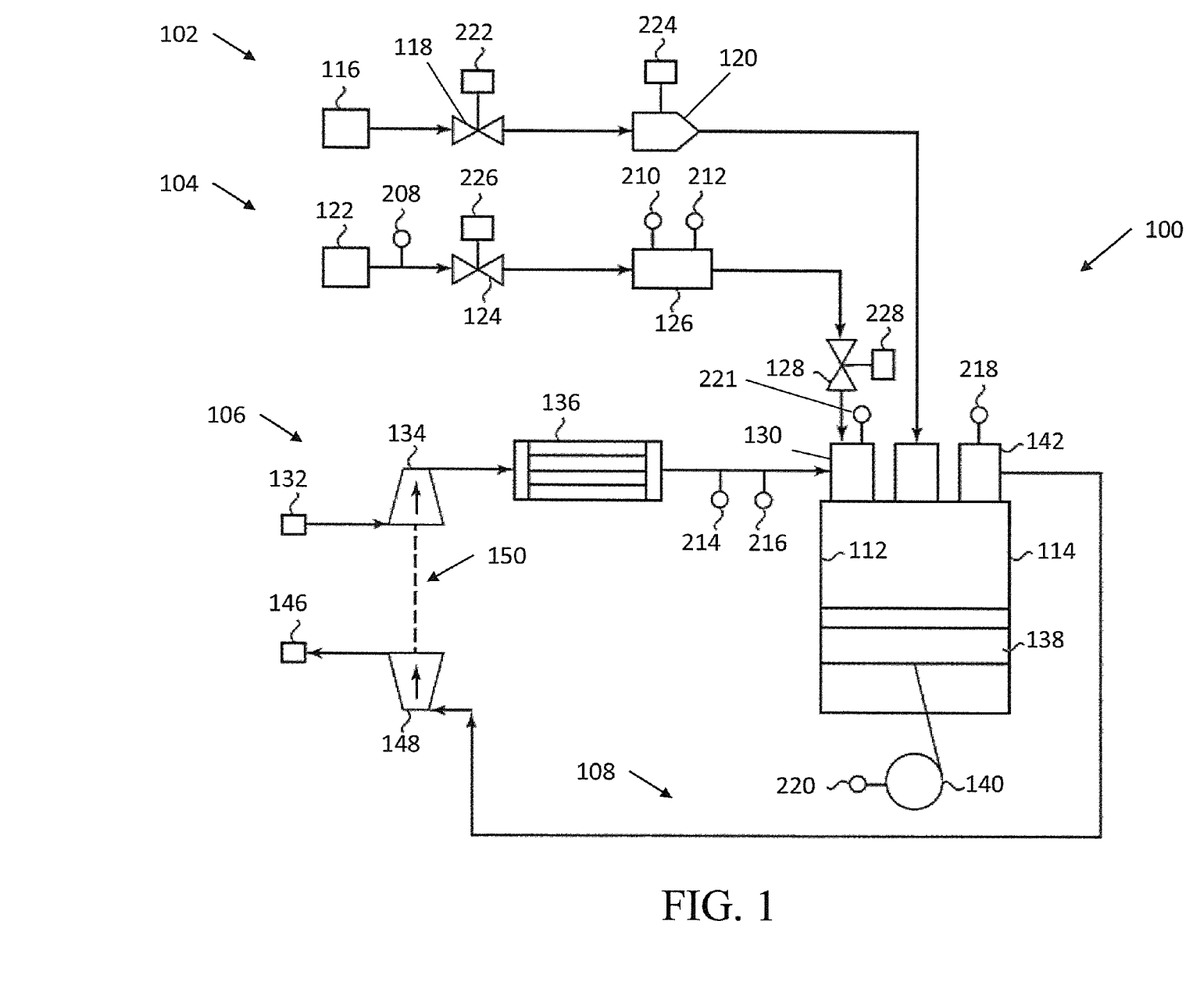
FIG. 1 is a schematic view of an engine system, according to one embodiment.

FIG. 1 illustrates a schematic of a dual fuel engine system 100, according to one aspect of the disclosure. In this view, the dual fuel engine system 100 is shown illustrating two fuel lines, including a diesel supply line 102 and a gaseous fuel supply line 104, an air intake line 106, and an exit exhaust line 108. Air and fuel flow through the system 100 into the cylinder 112. After entering the cylinder 112, the diesel fuel may self-ignite, which in turn may ignite the fuel in an ignition mechanism (not shown), which may be coupled to the engine housing 114. After the combustion process, the exhaust gases exit along the exit exhaust line 108.

The diesel supply line 102 may include a diesel supply tank, 116, fuel control valve 118, and a fuel pump 120. The diesel supply line 102 may include other components including filters, rack control valves, relief valves, or the like, none of which are shown. The fuel pump 120 is disposed along the diesel supply line 102 downstream of the diesel fuel supply 116. The fuel pump 120 may pump diesel fuel into the cylinder 112 of the engine. It should be appreciated that a rail type system, also referred to as a common rail, or a fuel manifold may be used to supply diesel fuel to the cylinder 112.

The gaseous supply line 104 may include a gaseous fuel supply 122, a fuel pressure regulator or valve 124, a gas rail 126, and a gas admission valve or injector 128. It should be appreciated that other fuel line components may be used in the gaseous supply line 104. The gaseous fuel supply 122 may include a liquefied fuel tank, a cryogenic pump, and other such elements as are commonly used and known in the art. The pressure regulator 124 may receive gaseous fuel from the gaseous fuel supply 122 prior to the fuel entering the gas rail 126. The gaseous fuel enters the gas rail 126 under pressure from the fuel supply 122 when the pressure regulator 124 is in an open position. The fuel exits the gas rail 126 and enters the fuel injector 128, where the fuel is selectively controlled and timed before entering the intake manifold 130. The intake manifold 130 may be coupled to an engine housing 114 and supplies intake air as well as gaseous fuel to each cylinder 112 by way of appropriate intake valves (not shown).

The air intake line 106 includes an air inlet 132, a compressor 134, and an aftercooler 136. In other embodiments, the air intake line 106 may include one or more valves for various purposes including for controlling the intake pressure into the engine 100. The air inlet 132, which may include a filter, supplies intake air to the air intake line 106. The intake air is conveyed to and past the compressor 134, through the aftercooler 136, into the intake manifold 130 where it is combined with the gaseous fuel, and into the engine cylinder 112.

After the diesel fuel and/or the air and gaseous fuel mixture flow through their corresponding supply lines, they enter the cylinder 112. The cylinder 112 is located within the engine housing 114 along with a piston 138. The piston 138 is movable within cylinder 112 between a top dead center position and a bottom dead center position in a conventional manner to induce rotation of a crankshaft 140. It should be appreciated that there may be additional cylinders which are not shown in FIG. 1, commonly six, eight, twelve or more cylinders, each having a piston reciprocable therein to contribute to the rotation of the crankshaft 140. During a combustion process, the diesel fuel may self-ignite, which in turn may ignite the gaseous fuel, thereby driving the piston 138 and inducing rotation of the crankshaft 140.

After the combustion process, the exhaust created during combustion flows along the exhaust line 108 from an exhaust manifold 142 to an exhaust outlet 146. In an embodiment, a turbine 148 is part of a turbocharger 150 and positioned between the exhaust manifold 142 and the exhaust outlet 146. The compressor 134 may also be part of the turbocharger 150.

Figure 2:
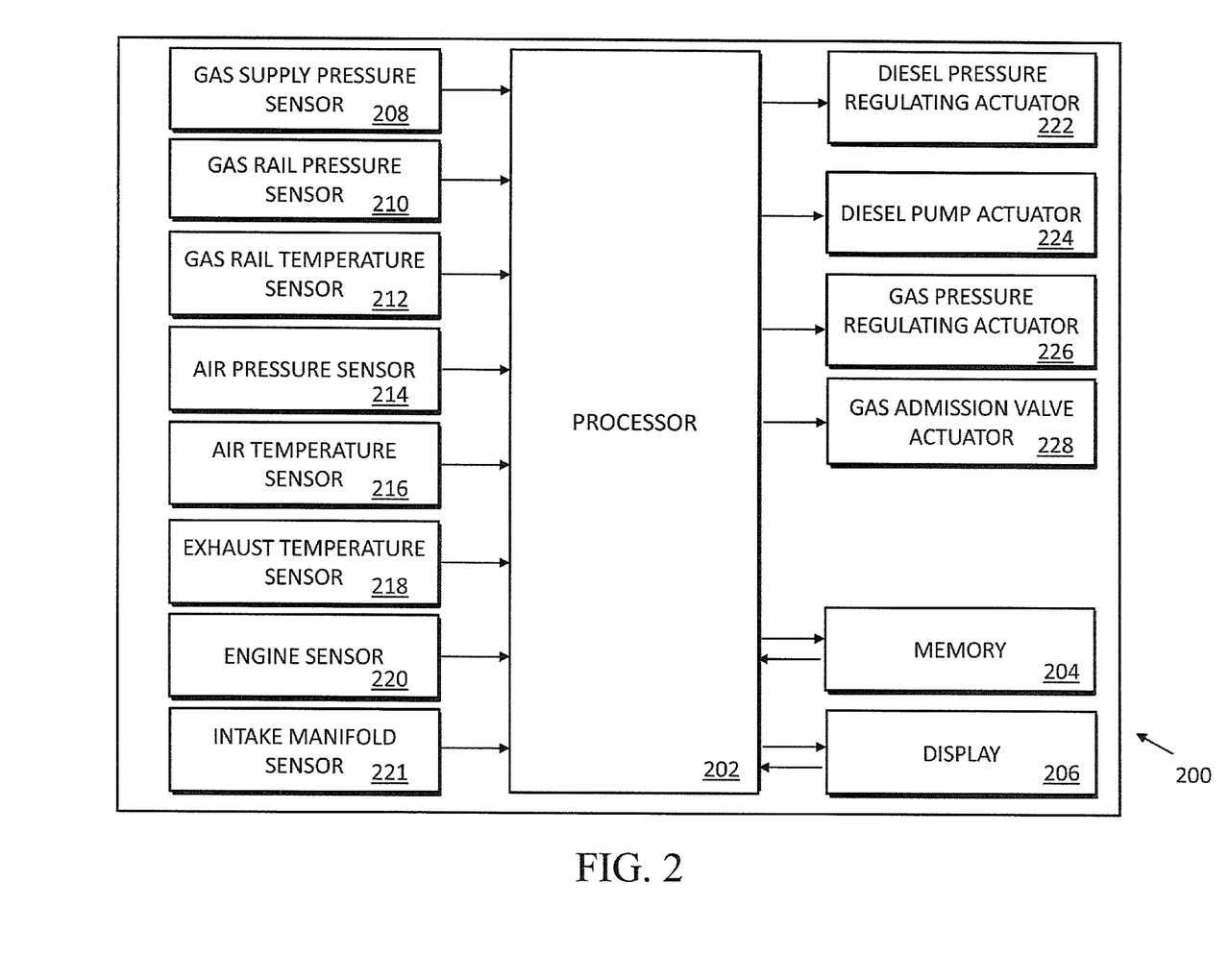
FIG. 2 is a schematic view of a controller, according to one embodiment.

FIG. 2 illustrates a controller 200, such as an electronic control unit, which may be used to facilitate control and coordination of the dual fuel system 100. In this embodiment, the controller comprises each sensor and actuator located within the disclosed fuel system 100. Additionally, the controller 200 includes a processor 202, memory 204, and a display 206. While the controller 200 is represented as a single unit, in other aspects the controller 200 may be distributed as a plurality of distinct but interoperating units, incorporated into another component, or located at different locations on or off the dual fuel system 100.

Referring to FIG. 1, the gaseous fuel line 104 may include a supply pressure sensor 208, a gas rail pressure sensor 210, and a gas rail temperature sensor 212. The supply pressure sensor 208 may be configured to monitor the pressure of the gaseous fuel coming from the fuel supply 122 and entering the fuel pressure regulator 124. As the gaseous fuel pressure is sensed, a signal representing a sensed value may be sent to the processor 202 and recorded in memory 204. The gas rail pressure sensor 210 and gas rail temperature sensor 212 sense the pressure and temperature of the fuel within the gas rail 126. The sensors may be configured to sense pressure and temperature over a period of time and record the data in memory 204.

The air fuel line 106 may include an air temperature sensor 214 and an air pressure sensor 216. These sensors may be configured to monitor the temperature and pressure of the air prior to entering the intake manifold 130. The intake manifold 130 may include an intake manifold sensor 221 coupled thereto. The manifold sensor 221 may be configured to monitor a parameter indicative of a pressure of a mixture of the gaseous fuel and air. The manifold sensor 221 may be a conventional intake manifold pressure sensor.

The fuel system 100 may also include an exhaust temperature sensor 218 and an engine sensor 220. The exhaust temperature of the engine may be used as a parameter in the determination of the air-to-fuel ratio of the fuel. The engine sensor 220 may be used to determine the speed and load of the crankshaft 140. In other embodiments, additional sensors may be used.

As illustrated in FIG. 2, the data processor 202 may be coupled to each of the sensors and actuators. The processor 202 may be configured to output signals that are responsive to inputs from the sensors and to control the various components of the engine 100 through the actuators, as further described herein. A display 206 may also be coupled to the processor 202 to display various data to an operator relating to the temperature, pressure, flow rate, or still other parameters. Action may be taken in response to the data, specifically the mass flow rate of the gaseous fuel, including modifying the fuel supplied to the gaseous fuel line 104 to maintain an appropriate air to fuel ratio. The actuators may include a diesel pressure regulating actuator 222, a diesel pump actuator 224, a gas pressure regulating actuator 226, and a gas admission valve actuator 228 coupled to the fuel control valve 118, diesel pump 120, pressure regulator 124, and fuel injector 128, respectively. In other embodiments, additional actuators may be used.

The processor 202 utilizes the values sensed by the sensors that may be stored in computer readable memory 204 to determine the specific gravity and mass flow rate of the gaseous fuel using algorithms stored in the memory 204. The processor 202 may compare the determined mass flow rate to a threshold value, i.e. emission standards, that may be stored in memory 204 or input into the controller 200 by an input device (not shown). If the determined mass flow rate meets or exceeds the maximum threshold, the processor 202 may send signals to the diesel fuel line actuators 222, 224 and/or the gaseous fuel line actuators 226, 228 to adjust the fuel flow rates accordingly. If the mass flow rate has not reached the threshold, then the processor 202 may or may not send signals to the diesel fuel line actuators 222, 224 and/or the gaseous fuel line actuators 226, 228 adjusting the fuel flow rates. In either case the processor 202 may also send signals to the display 206 indicating whether the mass flow rate has exceeded or has yet to exceed the threshold.

The computer readable memory 204 may include random access memory (RAM) and/or read-only memory (ROM). The memory 204 may store computer executable code including an algorithm for determining the specific gravity value of the gaseous fuel. The memory 204 may also store various digital files including the values sensed by the various sensors. The information stored in the memory 204 may be provided to the processor 202 so that the processor may determine the specific gravity of the gaseous fuel.

Figure 3:
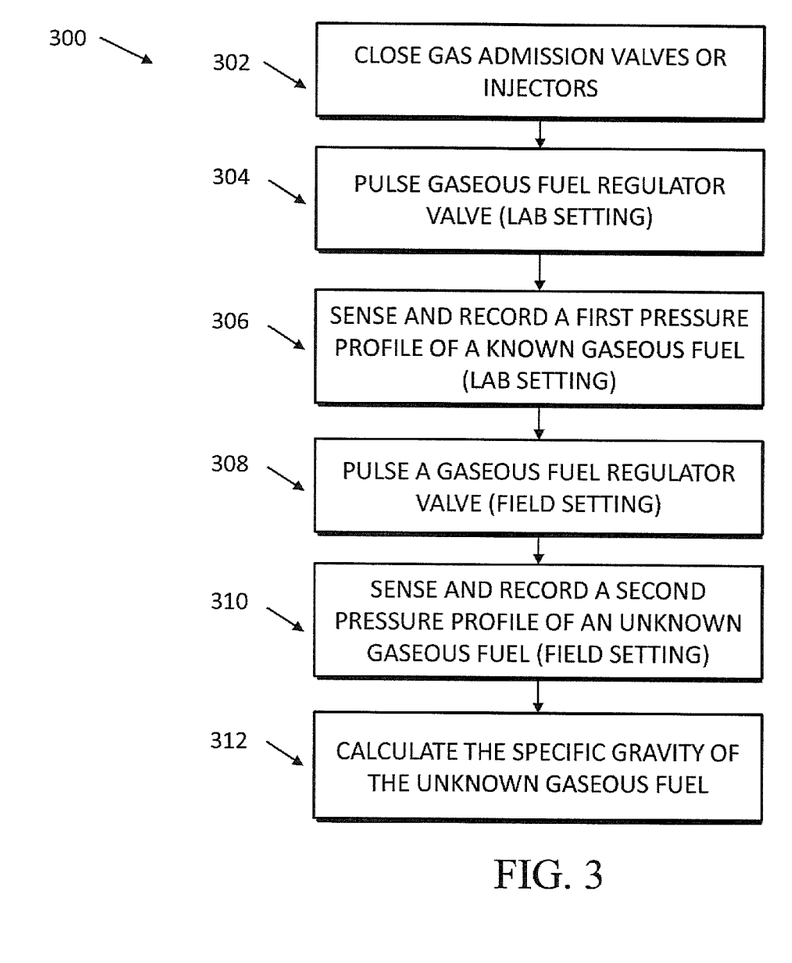
FIG. 3 is a flowchart depicting a method of determining the specific gravity of an unknown fuel.

FIG. 3 is a flowchart depicting a method, 300, for determining the specific gravity of an unknown gaseous fuel within a dual fuel engine, according to an embodiment of this disclosure. By comparing the specific gravity and pressure of a known gaseous fuel, i.e. natural gas, with the pressure of an unknown gaseous fuel, the processor 202 may be configured to calculate the specific gravity of the unknown gaseous fuel. This method may occur prior to the combustion of the gaseous fuel.

In step 302, the gas admission valve 128 is completely closed, restricting gaseous fuel from entering the intake manifold 130, and therefore, the engine cylinder 112. This is common when an engine is running in diesel mode in a dual fuel engine. Since the gaseous fuel is restricted from entering the cylinder 112, only the diesel fuel may enter the cylinder 112 and drive the piston 138.

In step 304, when the gas admission valve 128 is closed, the gaseous fuel regulator valve 124 is pulsed. This step is performed in a laboratory setting with a known gaseous fuel, i.e. natural gas. During this step, the processor 202 may be configured to pulse the fuel regulator valve 124 by operating the fuel regulator valve 124, via the valve actuator 226, from a closed position to an open position, and back to a closed position. While the fuel regulator valve 124 is in the open position, gaseous fuel is injected into the gas rail 126. Once the valve 128 is operated back to the closed position, no fuel either enters or exits the gas rail 126.

In step 306, during the pulse event and for a predetermined time after, the gas rail pressure sensor 210 may be configured to sense pressure values of the gaseous fuel within the gas rail 126. The pressure values that are sensed may make up a first pressure profile. The first pressure profile may include one or many pressure values. The processor 202 may be configured to store and record these pressure values in memory 204. This step may be performed in a laboratory setting. The values stored during step 306, the first pressure profile, may be referred to as reference values.

In another embodiment, reference values may have been previously determined and stored in memory 204 prior to determining the specific gravity of an unknown gaseous fuel. For example, the reference values may comprise a reference pressure profile. When calculating the specific gravity, the processor 202 may be configured to access the stored reference values.

After step 306, the known gaseous fuel is removed or substantially removed from the gas rail 126. In step 308, the gaseous fuel regulator valve 124 is pulsed a second time, whereby the processor 202 may be configured to operate the fuel regulator valve 124, via the valve actuator 226, from a closed position to an open position, and back to a closed position. This step is performed in a field setting with an unknown gaseous fuel. A field setting may include the dual fuel system 100 operating under normal conditions. An unknown gaseous fuel may be defined as a fuel which has properties, i.e. specific gravity, that are not known. It should be appreciated that this method may be performed using a fuel which has known properties for various purposes such as verification or calibration. While the fuel regulator 124 is in the open position, the unknown gaseous fuel is injected into the gas rail 126.

In step 310, during the second pulse event and for a predetermined time after, the gas rail pressure sensor 210 may be configured to sense pressure values of the unknown gaseous fuel within the gas rail 126. These pressure values may make up a second pressure profile. The second pressure profile may include one or many pressure values. The total time period for the second pulse event and the predetermined time period after the second pulse event may be the same total time period as the time period for the first pulse event and the predetermined time period after the first pulse event, respectively. The processor 202 may be configured to store and record the second pressure profile in memory 204. Step 310 may also be performed in a field setting.

At step 312, after the first and second pressure profiles have been recorded in a memory 204, the specific gravity of the unknown fuel may be calculated by using the first and second pressure profiles along with the specific gravity of the known gaseous fuel. An equation that may be stored in memory 204 and used to calculate specific gravity is as follows:

$$\text{SpGrav}_{UNKNOWN} = \text{SpGrav}_{KNOWN} * (P_1/P_2) \quad \text{Equation 1:}$$

where $\text{SpGrav}_{UNKNOWN}$ is the specific gravity of the unknown fuel, $\text{SpGrav}_{KNOWN}$ is the specific gravity of the known fuel, $P_1$ is the first pressure profile, and $P_2$ is the second pressure profile. In this embodiment, the ratio of the first profile to the second profile is used along with the known specific gravity, $\text{SpGrav}_{KNOWN}$, of the known fuel to calculate the unknown specific gravity, $\text{SpGrav}_{UNKNOWN}$.

Another method for calculating the specific gravity may include sensing and recording a supply fuel pressure by the gas supply pressure sensor 208. An equation that may be stored in memory 204 and used to calculate specific gravity using supply pressures is as follows:

$$\text{SpGrav}_{UNKNOWN} = \text{SpGrav}_{KNOWN} * (P_1/P_2) * (S_2/S_1) * (T_2/T_1) \quad \text{Equation 2:}$$

where $\text{SpGrav}_{UNKNOWN}$ is the specific gravity of the unknown fuel, $\text{SpGrav}_{KNOWN}$ is the specific gravity of the known fuel, $P_1$ is the first pressure profile, $P_2$ is the second pressure profile, $S_1$ is the supply pressure of the known fuel, $S_2$ is the supply pressure of the unknown fuel, $T_1$ is the temperature profile of the known fuel, and $T_2$ is the temperature profile of the unknown fuel. In this embodiment, the ratio of the first profile pressure to the second profile pressure, the ratio of the second supply pressure to the first supply pressure, and the ratio of the second temperature profile to the first temperature profile are used to calculate the unknown specific gravity. Further, the first pressure profile, $P_1$, may be for the known fuel and the second pressure profile, $P_2$, may be for the unknown fuel. The supply pressure of the known fuel, $S_1$, may be determined by sensing the known fuel immediately prior to the first pulse step, ie. prior to step 304. The supply pressure of the unknown fuel, $S_2$, may be determined by sensing the unknown fuel immediately prior to the second pulse event, ie. prior to step 308. It should be appreciated that in other embodiments, the supply pressures may be computed at different times prior to the pulse events rather than immediately prior. The temperature profile, $T_1$, of the known fuel may be determined by sensing the temperature of the known fuel during the pulse event, ie. at step 306. The temperature profile, $T_2$, of the unknown fuel may be determined by sensing the temperature of the unknown fuel during a second pulse event, ie. at step 310. Each temperature profile, $T_1$ and $T_2$, may be sensed using the gas rail temperature sensor 212.

In other embodiments, the unknown specific gravity may also be determined by comparing the stored reference values of a known fuel to the sensed values of the unknown fuel. This may be performed by using a relationship between the reference data for the known fuel and the data sensed and recorded for the unknown fuel.

Figure 4:
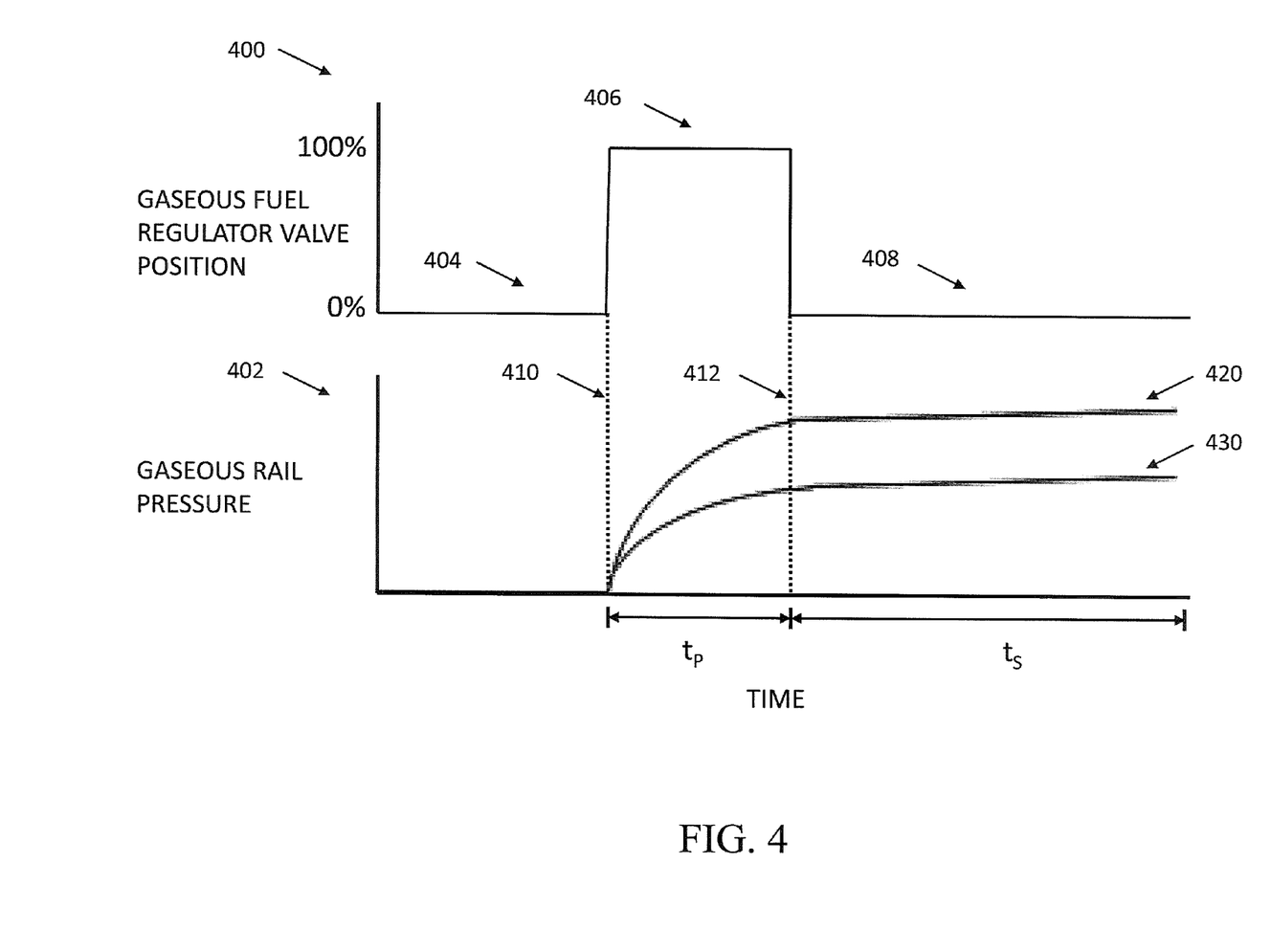
FIG. 4 is a graph illustrating the position of a valve, a first pressure profile, and a second pressure profile.

FIG. 4 includes two graphs, the first graph, 400, illustrates the position of a fuel regulator valve 124 and the second graph, 402, illustrates a first pressure profile, 420, and a second pressure profile, 430, of two different gaseous fuels.

Each graph illustrates the time period before, during, and after pulse events. It should be appreciated that the curves illustrated in graphs 400 and 402 are merely for exemplary purposes.

The upper graph, 400, illustrates the position of the fuel regulator valve 124, whereby 0% represents the valve 124 in the completely closed position, and 100% represents the valve 124 in the completely open position. At position 404, the fuel regulator valve 124 is in the closed position. This represents the position of the valve 124 prior to a pulse event, ie. prior to steps 304 and 308 of method 300. At position 406, the valve 124 has been operated open to 100%, allowing fuel to enter into the gas rail 126. The length of time the valve 124 is in the open position represents the time period of the pulse event, $t_p$. In other embodiments, the open position of the valve 124 may be less than 100%. Position 408 represents the position of the valve 124 after a pulse event, ie. after steps 304 and 308 of method 300, whereby the valve 124 is in the closed position.

The bottom graph, 402, in FIG. 4 illustrates a first pressure profile, 420, and a second pressure profile, 430, of two gaseous fuels. At time step 410, the pulse event may begin when the valve 124 is operated from the closed position to the open position. Once the valve 124 is operated to the open position, a fuel is injected into the gas rail 126 for a time period, $t_p$, and the fuel pressure increases. At time step 412, the valve 124 is operated back to the closed position, whereby fuel is no longer injected into the gas rail 126. After the valve 124 has been closed, it may take a period of time, $t_s$, for the pressure of the fuel within the gas rail 126 to stabilize. This process may be performed for each pulse event, 304 and 308 of method 300, for the known and unknown fuel to determine the first and second pressure profiles $P_1$ and $P_2$.

The first pressure profile, $P_1$, and the second pressure profile, $P_2$, as used in Equations 1 and 2, may be approximated by various methods to simplify the calculation for the specific gravity of the unknown fuel. A first method includes calculating a first pressure by computing the average of a range of values of the first pressure profile, $P_1$. The range of values may include the pressure values recorded after the fuel regulator valve 124 closes at the end of the pulse event, ie. at time step 412, and up until a predetermined amount of time thereafter. The predetermined amount of time may depend on the length of time for the pressure of the fuel to substantially stabilize, $t_s$; however, it should be appreciated that the predetermined amount of time may vary from the time to stabilize. A second pressure may be calculated by taking the average of a range of values of the second pressure profile, $P_2$. The range of values may include the pressure values recorded after the fuel regulator valve 124 closes, at the end of the pulse event, ie. at time step 412, and up until a predetermined amount of time thereafter. The first and second pressure values may then be substituted in for the pressure profiles, $P_1$ and $P_2$, of Equations 1 and/or 2 to calculate the unknown specific gravity. In a preferred embodiment, the ranges of values used in determining average pressure values for the first and second pressure profile are for equivalent time periods.

Another method for approximating the first pressure profile, $P_1$, and the second pressure profile, $P_2$, as used in Equations 1 and 2 may include obtaining a first instantaneous pressure value and a second instantaneous pressure value. The first instantaneous value may be obtained from a specific time step within the first pressure profile, $P_1$, which may be at the time the fuel regulator 124 closes, ie. at time step 412, or at a predetermined time thereafter. A second instantaneous value may be obtained from a specific time step within the second pressure profile, $P_2$, which may be at the time the fuel regulator 124 closes, ie. at time step 412, or at a predetermined time thereafter. In an embodiment, the second instantaneous value is taken from the same time step of the second pressure profile as the first instantaneous value taken from the first pressure profile. The first and second instantaneous pressure values may then be substituted in for the pressure profiles, $P_1$ and $P_2$, of Equations 1 and/or 2 to calculate the unknown specific gravity.

Another method for approximating the first pressure profile, $P_1$, and the second pressure profile, $P_2$, as used in Equations 1 and 2 may include integrating the first pressure profile, $P_1$, and the second pressure profile, $P_2$. This may include calculating a first pressure value by integrating the first pressure profile, $P_1$, over a first period of time. The first period of time may include the range from the start of the pulse event, ie. at time step 410, up until a predetermined time thereafter. A second pressure value may be calculated by integrating the second pressure profile, $P_2$, over a second period of time. In an embodiment, the first period of time and the second period of time are for the same length of time. The first and second pressure values may then be substituted in for the pressure profiles, $P_1$ and $P_2$, of Equations 1 and/or 2 to calculate the unknown specific gravity.

Once the pressure profiles are determined, the specific gravity of the unknown fuel may be calculated by the processor 202 and may be recorded in memory 204. Additionally, the processor 202 may send a signal to the display 206 and may send signals to the actuators to adjust the fuel flow through the system 100.

INDUSTRIAL APPLICABILITY

The present disclosure provides an advantageous system and method for calculating the specific gravity of an unknown gaseous fuel used in a dual fuel engine. An accurate determination may enable the fuel system to maintain the air to fuel ratio required to meet emission standards. If the specific gravity of the unknown gaseous fuel is determined, then an appropriate fuel mass flow through the gaseous supply line 104 may also be determined. Further, if the lower heating value of the unknown gaseous fuel is known, the air flowing through the air flow line 106 may be set to be proportional to the fuel mass flow. If the lower heating value of the unknown gaseous fuel is different from the lower heating value of a known gaseous fuel, then the energy content in the same mass flow of the unknown gaseous fuel is different from the known gaseous fuel, which may be taken into account to set the air flow. Thereafter, the air to fuel ratio may be determined from the fuel mass flow and the air flow.

While the disclosure is described herein using a limited number of embodiments, these specific embodiments are not intended to limit the scope of the disclosure as otherwise described and claimed herein. Modification and variations from the described embodiments exist. More specifically, the following examples are given as a specific illustration of embodiments of the claimed disclosure. It should be understood that the invention is not limited to the specific details set forth in the examples.

We claim:

1. A method for determining the specific gravity of a fuel used in a fuel engine including a fuel regulator valve and a fuel rail, comprising:

sensing a pressure profile of a fuel having a specific gravity with at least one sensor; and calculating the specific gravity of the fuel, with a processor, based on the pressure profile, a reference pressure profile, and a reference specific gravity,
pulsing the fuel regulator valve; and
injecting the fuel into the fuel rail,
wherein the pressure profile of the fuel is sensed when the fuel is in the fuel rail,
wherein calculating the specific gravity of the fuel further comprises using a ratio of a supply pressure of the fuel to a reference supply pressure,
wherein the supply pressure of the fuel is the pressure of the fuel prior to being injected into the fuel rail.

2. The method of claim 1, wherein calculating the specific gravity of the fuel further comprises:
calculating a pressure value of the fuel based on the average of a range of values of the pressure profile of the fuel;
calculating the specific gravity of the fuel by using the ratio of a reference pressure value to the pressure value, wherein the reference pressure value is the average of a range of values of the reference pressure profile.

3. The method of claim 1, wherein calculating the specific gravity of a fuel further comprises:
determining a pressure value based on an instantaneous value of the pressure profile of the fuel; and
calculating the specific gravity of the fuel by using the ratio of a reference pressure value to the pressure value, wherein the reference pressure value is an instantaneous value of the reference pressure profile.

4. The method of claim 1, wherein calculating the specific gravity of a fuel further comprises:
calculating a pressure value by integrating the pressure profile of the fuel over a first time period; and
calculating the specific gravity of the fuel by using the ratio of a reference pressure value to the pressure value, wherein the reference pressure value is determined by integrating the reference pressure profile of a second period of time, wherein the first time period and the second time period are for the same length of time.

5. The method of claim 1, further comprising recording the pressure profile of the fuel in at least one memory.

6. The method of claim 1, wherein the reference pressure profile and the reference specific gravity are stored in at least one memory.

7. The method of claim 1, wherein the reference pressure profile and the reference specific gravity are based on a reference fuel having a known specific gravity.

8. The method of claim 1, wherein the reference pressure profile comprises pressure values over a first time period and the pressure profile of the fuel comprises pressure values sensed over a second time period, wherein the first time period and the second time period are the same length of time.

9. The method of claim 1, wherein calculating the specific gravity of the fuel further comprises using a ratio of the reference pressure profile to the pressure profile of the fuel.

\* \* \* \* \*